United States Patent
Mattson et al.

(10) Patent No.: US 6,476,051 B2
(45) Date of Patent: Nov. 5, 2002

(54) ANTIPSYCHOTIC HETEROCYCLE COMPOUNDS

(75) Inventors: Ronald J. Mattson, Meriden; Joseph P. Yevich, Southington; Jun Yuan, Guilford; Arlene S. Eison, Killingworth; Derek Denhart, Wallingford, all of CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/735,384

(22) Filed: Dec. 12, 2000

(65) Prior Publication Data

US 2002/0072611 A1 Jun. 13, 2002

Related U.S. Application Data

(60) Provisional application No. 60/172,200, filed on Dec. 17, 1999.

(51) Int. Cl.[7] ............... A61K 31/4439; C07D 401/12; C07D 401/14
(52) U.S. Cl. ............ 514/321; 514/323; 514/338; 546/198; 546/201; 546/270.1
(58) Field of Search ............... 514/323, 321, 514/338; 546/198, 201, 270.1

(56) References Cited

U.S. PATENT DOCUMENTS

| | | |
|---|---|---|
| 4,530,932 A | 7/1985 | Clemence et al. |
| 5,521,197 A | 5/1996 | Audia |
| 5,627,196 A | 5/1997 | Audia et al. |
| 5,741,789 A | 4/1998 | Hibschman et al. |

FOREIGN PATENT DOCUMENTS

| | | | |
|---|---|---|---|
| EP | 0714894 A1 | 6/1996 | |
| EP | 0830864 A1 | 3/1998 | |
| WO | 97/23215 | * | 7/1997 |
| WO | WO98/06402 | 2/1998 | |
| WO | WO98/11895 | 3/1998 | |
| WO | WO98/28293 | 7/1998 | |

OTHER PUBLICATIONS

Hiroyuki Obase, et al., "New Antihypertensive Agents. II. Studies on New Analogs of 4–Piperidylbenzimidazolinones," *Chem. Pharm. Bull.*, vol. 30, 1982, pp. 474–483.

Hiroyuki Obase, et al., "Synthesis and Adrenergic β–Blocking Activity of Some Propanolamine Derivatives," *Chem. Pharm. Bull.*, vol. 26, 1978, pp. 1443–1452.

Von A. Franke, et al., "Neue β–Sympatholytika: Synthesen und pharmakologische Wirkung isomerer Benzthiazol–und Benzoxazol–Derivate," *Arzneim.–Forsch.*, No. 11, 1980, pp. 1831–1838.

* cited by examiner

*Primary Examiner*—Ceila Chang
*Assistant Examiner*—Sonya Wright
(74) *Attorney, Agent, or Firm*—Richard P. Ryan

(57) ABSTRACT

Compounds of Formula I:

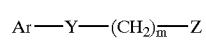

wherein Ar, Y, m, and Z are as defined in the specification, are useful antipsychotic and antidepressant agents demonstrating potent inhibition of 5-HT reuptake and dopamine D2 receptor antagonism.

9 Claims, No Drawings

ANTIPSYCHOTIC HETEROCYCLE COMPOUNDS

CROSS REFERENCE TO RELATED APPLICATIONS

This non-provisional application claims priority from provisional application U.S. Ser. No. 60/172,200 filed Dec. 17, 1999.

BACKGROUND OF THE INVENTION

This invention pertains to cyclic amino derivatives having psychotropic and bio-affecting properties and to their preparation and use in treating patients suffering from or susceptible to psychosis, acute mania, mild anxiety states, or depression in combination with psychotic episodes by the administration of these cyclic amino derivatives. More specifically, the invention is concerned with the medicinal use of compounds having benzene or benzothiazole rings linked by sidechains to the nitrogen atom of 4-substituted-1,2,5,6-tetrahydropyridine and -piperidine moieties. These compounds possess unique dopaminergic and serotonergic profiles that make them useful in the treatment of psychosis and other mental illnesses caused by disorders of the dopaminergic and serotonergic systems.

The combination of a serotonin reuptake inhibitor, such as fluoxetine, with a dopaminergic antipsychotic agent, such as olanzapine, has been described as an improved treatment for psychosis, (European Patent Application 830864, published Sep. 22, 1997).

The preparation and use of tetrahydropyridinyl- and piperidinylindoles, 1, and related compounds as serotonin 5-HT$_{1F}$ agonists for the treatment of migraine, allergic rhinitis, and associated diseases has been described. Cf: U.S. Pat. No. 5,521,197 (May 28, 1996), WO Patent Publication No. 9811895 (Mar. 26, 1998) and WO 9806402 (Feb. 19, 1998), and European Patent Application 714894 (Jun. 5, 1996).

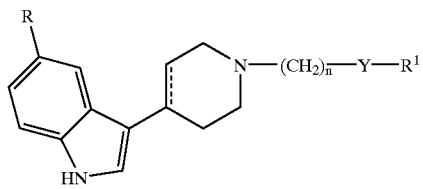

1

In 1, Y=O, S, or a bond, and R$^1$ is naphthyl, phenyl, substituted phenyl, halo, alkyl, alkylthio, alkoxy, benzyloxy, OH, CONH$_2$.

A series of aryloxy propanolamines, including compound 2, was disclosed by Obase, et al., in *Chem. Pharm. Bull.*, 30(2), 474–83, 1982, as antihypertensive agents.

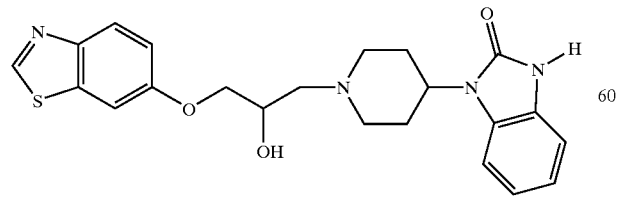

2

The synthesis and adrenergic β-blocking activity of some non-cyclic amine derivatives; e.g., 3, has been described by Obase, et al., *Chem. Pharm. Bull.*, 26(5), 1443–52, 1978, and by Franke, et al., *Arzneim.-Forsch.*, 30(11), 1831–8, 1980.

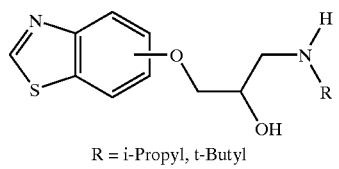

3

R = i-Propyl, t-Butyl

Some derivatives of 4-(1H-indol-3-yl)-1 piperidineethanol derivatives, 4, having antiarrhythmic activity were described by Clemence, et al., in U.S. Pat. No. 4,530,932 (Jul. 23, 1985).

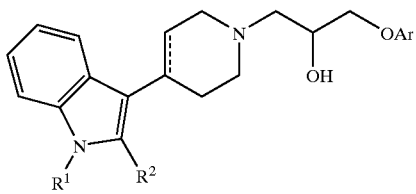

4

In 4, Ar is aryl or a selected group of heteroaryl moieties not including benzothiazole.

The preparation and use of indane and dihydroindole derivatives of indolylpiperidine compounds, 5, as dopamine D$_4$ receptor, 5-HT receptor, and 5-HT transporter ligands was described in WO Patent Publication No. 9828293 (Jul. 2, 1998).

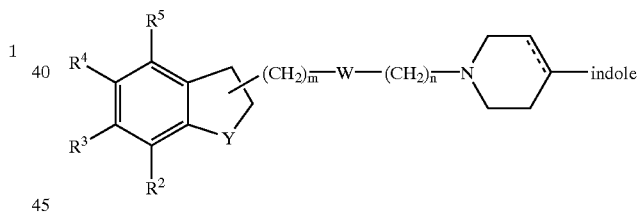

5

In sum, none of these references suggest the novel compounds of the present invention.

A series of nitrogen-containing heterocycles linked by oxygen to alkanamines comprising, inter alia, compounds of formula 6, were disclosed and claimed for the treatment of conditions related to the reuptake of serotonin and by the 5-HT$_{1a}$ receptor (U.S. Pat. No. 5,741,789, Apr. 21, 1998, and U.S. Pat. No. 5,627,196, May 6, 1997). In formula 6, D represents a nitrogen-containing residue that completes

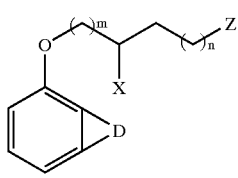

6 fused pyrrolo, imidazolo, pyrido, pyrazino, pyridazino, or pyrimido moieties.

Z can be

with R² being absent when a double bond is intended or being hydrogen or a substituent, including a benzyl group. R³ is a non-hydrogen substituent that can be indole.

SUMMARY OF THE INVENTION

In its broadest aspect, the invention is concerned with the use of certain benzene or benzothiazole compounds linked by sidechains to indolyl-1,2,5,6-tetrahydropyridines and -piperidines or substituted 4-benzylpiperidines. These compounds possess a unique dopaminergic and serotonergic profile useful for treating CNS disorders such as psychosis and depression and they conform to Formula I:

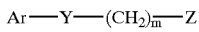

In Formula I:
Ar is selected from

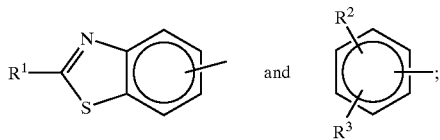

Z is II or III;

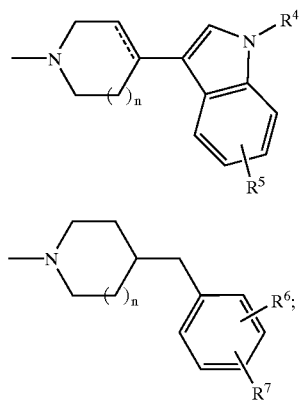

Y is sulfur or oxygen;
$R^1$ and $R^4$ are independently selected from H and lower alkyl;
$R^2$, $R^3$, $R^6$ and $R^7$ are independently selected from H, halogen, and lower alkoxy;
$R^5$ is selected from H, halogen, lower alkoxy and cyano;
m is an integer from 2–6;
n is zero or the integer 1 or 2; and
a dotted line represents an optional double bond.

"Halo" or "halogen" refers to fluoride, chloride, bromide or iodide substituents with fluoride, chloride and bromide preferred.

"Lower" refers to an alkyl or alkoxy group having from one to four carbon atoms.

Additionally, compounds of Formula I also encompass all pharmaceutically acceptable acid addition salts and/or solvates thereof. The present invention is also considered to include stereoisomers including geometric as well as optical isomers, e.g. mixtures of enantiomers as well as individual enantiomers and diastereomers, which arise as a consequence or structural asymmetry in certain compounds of the instant series. Separation of the individual isomers is accomplished by application of various methods which are well known to practitioners in the art.

Several classes of Formula I compounds are intended and result from selection among benzene, benzothiazole, and II and III structural moieties. The benzothiazole classes of compounds are novel.

Preferred compounds are those wherein m is 3, n is 1 and Y is oxygen.

Preferred compound examples where Z is Formula II are shown below.

A. Benzothiazole Derivatives

5-{3-[4-(5-fluoroindol-3-yl)-1,2,5,6-tetrahydropyrid-1-yl]propoxy}-2-methylbenzothiazole;
5-{3-[4-(5-cyanoindol-3-yl)-1,2,5,6-tetrahydropyrid-1-yl]propoxy}-2-methylbenzothiazole;
5-{3-[4-(5-fluoroindol-3-yl)piperidinyl]propoxy}-2-methylbenzothiazole;
5-{3-[4-(5-cyanoindol-3-yl)piperidinyl]propoxy}-2-methylbenzothiazole;
5-{4-[4-(5-cyanoindol-3-yl)-1,2,5,6-tetrahydropyrid-1-yl]butoxy}-2-methylbenzothiazole;
5-{4-[4-(5-cyanoindol-3-yl)piperidinyl]butoxy}-2-methylbenzothiazole;
5-{3-[4-(5-bromoindol-3-yl)-1,2,5,6-tetrahydropyrid-1-yl]propoxy}-2-methylbenzothiazole;
5-{3-[4-(4-fluoroindol-3-yl)-1,2,5,6-tetrahydropyrid-1-yl]propoxy}-2-methylbenzothiazole;
5-{4-[4-(4-fluoroindol-3-yl)1,2,5,6-tetrahydropyrid-1-yl]butoxy}-2-methylbenzothiazole;
5-{5-[4-(4-fluoroindol-3-yl)-1,2,5,6-tetrahydropyrid-1-yl]pentoxy}-2-methylbenzothiazole;
5-{4-[4-(5-fluoroindol-3-yl)1,2,5,6-tetrahydropyrid-1-yl]butoxy}-2-methylbenzothiazole;
5-{5-[4-(5-fluoroindol-3-yl)-1,2,5,6-tetrahydropyrid-1-yl]pentoxy}-2-methylbenzothiazole;
5-{3-[4-(7-fluoroindol-3-yl)-1,2,5,6-tetrahydropyrid-1-yl]propoxy}-2-methylbenzothiazole;
5-{4-[4-(7-fluoroindol-3-yl)1,2,5,6-tetrahydropyrid-1-yl]butoxy}-2-methylbenzothiazole;
5-{5-[4-(7-fluoroindol-3-yl)-1,2,5,6-tetrahydropyrid-1-yl]pentoxy}-2-methylbenzothiazole;
5-{4-[4-(5-chloroindol-3-yl)1,2,5,6-tetrahydropyrid-1-yl]butoxy}-2-methylbenzothiazole;
5-{5-[4-(5-chloroindol-3-yl)-1,2,5,6-tetrahydropyrid-1-yl]pentoxy}-2-methylbenzothiazole;
5-{3-[4-(6-chloroindol-3-yl)-1,2,5,6-tetrahydropyrid-1-yl]propoxy}-2-methylbenzothiazole;
5-{4-[4-(6-chloroindol-3-yl)1,2,5,6-tetrahydropyrid-1-yl]butoxy}-2-methylbenzothiazole;
5-{5-[4-(6-chloroindol-3-yl)-1,2,5,6-tetrahydropyrid-1-yl]pentoxy}-2-methylbenzothiazole;
5-{3-[4-(6-bromoindol-3-yl)-1,2,5,6-tetrahydropyrid-1-yl]propoxy}-2-methylbenzothiazole;
5-{4-[4-(6-bromoindol-3-yl)1,2,5,6-tetrahydropyrid-1-yl]butoxy}-2-methylbenzothiazole;

5-{5-[4-(6-bromoindol-3-yl)-1,2,5,6-tetrahydropyrid-1-yl]pentoxy}-2-methylbenzothiazole;
5-{3-[4-(7-bromoindol-3-yl)-1,2,5,6-tetrahydropyrid-1-yl]propoxy}-2-methylbenzothiazole;
5-{4-[4-(7-bromoindol-3-yl)1,2,5,6-tetrahydropyrid-1-yl]butoxy}-2-methylbenzothiazole;
5-{5-[4-(7-bromoindol-3-yl)-1,2,5,6-tetrahydropyrid-1-yl]pentoxy}-2-methylbenzothiazole;
5-{3-[4-(5-methoxyindol-3-yl)-1,2,5,6-tetrahydropyrid-1-yl]propoxy}-2-methylbenzothiazole;
5-{4-[4-(5-methoxyindol-3-yl)1,2,5,6-tetrahydropyrid-1-yl]butoxy}-2-methylbenzothiazole; and
5-{5-[4-(5-methoxyindol-3-yl)-1,2,5,6-tetrahydropyrid-1-yl]pentoxy}-2-methylbenzothiazole.

B. Benzene Derivatives

3-[1-(3-phenoxypropyl)-4-piperidinyl]-5-cyanoindole;
3-{1-[3-(2-fluorophenoxy)propyl]-4-piperidinyl}-5-cyanoindole;
3-{1-[3-(4-fluorophenoxy)propyl]-4-piperidinyl}-5-cyanoindole;
3-{1-[3-(2-methoxyphenoxy)propyl]-4-piperidinyl}-5-cyanoindole;
3-{1-[3-(3-methoxyphenoxy)propyl]-4-piperidinyl}-5-cyanoindole;
3-{1-[3-(4-methoxyphenoxy)propyl]-4-piperidinyl}-5-cyanoindole; and
3-{1-[3-(3,4-dimethoxyphenoxy)propyl]-4-piperidinyl}-5-cyanoindole.

Preferred compound examples where Z is Formula III are shown below.

5-{3-[4-(2H-benzo[d]1,3-dioxolan-4-ylmethyl)piperidinyl]propoxy}-2-methylbenzothiazole;
5-(3-{4-[(2-bromo-5-methoxyphenyl)methyl]piperidinyl}propoxy)-2-methylbenzothiazole;
5-(3-{4-[(2-bromophenyl)methyl]piperidinyl}propoxy)-2-methylbenzothiazole;
5-(3-{4-[(2-bromo-5-fluorophenyl)methyl]piperidinyl}propoxy)-2-methylbenzothiazole;
5-(3-{4-[(2,-5-difluorophenyl)methyl]piperidinyl}propoxy)-2-methylbenzothiazole;
5-(3-{4-[(3-methoxyphenyl)methyl]piperidinyl}propoxy)-2-methylbenzothiazole;
5-(3-{4-[(2-chlorophenyl)methyl]piperidinyl}propoxy)-2-methylbenzothiazole; and
5-(3-{4-[(2,5-dichlorophenyl)methyl]piperidinyl}propoxy)-2-methylbenzothiazole.

The pharmaceutically acceptable acid addition salts of the invention are those in which the counter ion does not contribute significantly to the toxicity or pharmacological activity of the salt and, as such, they are the pharmacological equivalents of the bases of Formula I. They are generally preferred for medical usage. In some instances, they have physical properties which makes them more desirable for pharmaceutical formulation such as solubility, lack of hygroscopicity, compressibility with respect to tablet formation and compatibility with other ingredients with which the substance may be used for pharmaceutical purposes. The salts are routinely made by admixture of a Formula I base with the selected acid, preferably by contact in solution employing an excess of commonly used inert solvents such as water, ether, benzene, methanol, ethanol, ethyl acetate and acetonitrile. They may also be made by metathesis or treatment with an ion exchange resin under conditions in which the anion of one salt of the substance of the Formula I is replaced by another anion under conditions which allow for separation of the desired species such as by precipitation from solution or extraction into a solvent, or elution from or retention on an ion exchange resin. Pharmaceutically acceptable acids for the purposes of salt formation of the substances of Formula I include sulfuric, phosphoric, hydrochloric, hydrobromic, hydroiodic, citric, acetic, benzoic, cinnamic, fumaric, mandelic, phosphoric, nitric, mucic, isethionic, palmitic, heptanoic, and others.

Compounds of Formula I, where Z=II, are most conveniently synthesized by reacting (Reaction 1) intermediate IV (shown as a benzothiazole derivative), where X is a leaving group such as halogen, aryl- or alkyl-sulfonate, or the like, with amine V in a suitable solvent, such as acetonitrile, acetone, DMSO, DMF, and the like, with suitable bases, such as trialkyl amines or sodium, potassium, or cesium carbonate, or the like, under standard alkylation conditions using catalysts such as potassium iodide. In a similar manner in Reaction 2, intermediate IV can be reacted with amine VI to give compounds of Formula I where Z is III. Other methods known to those skilled in the art may also be used.

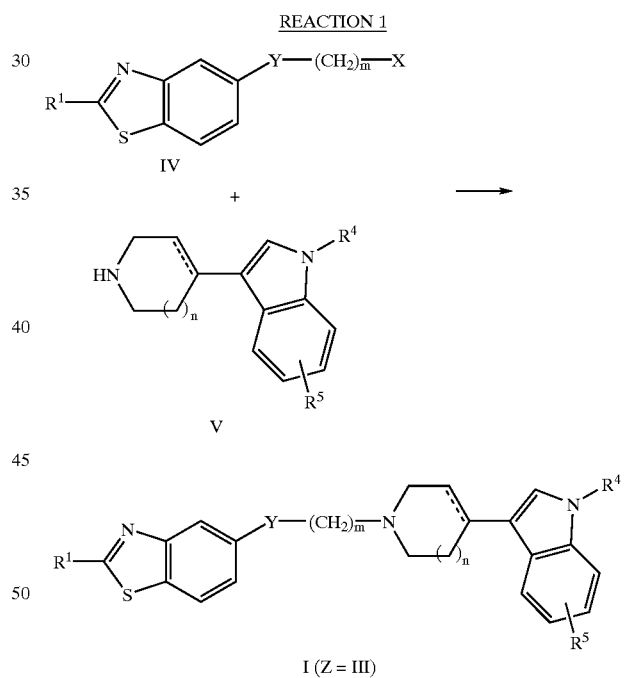

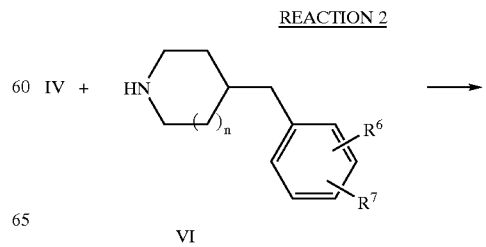

-continued

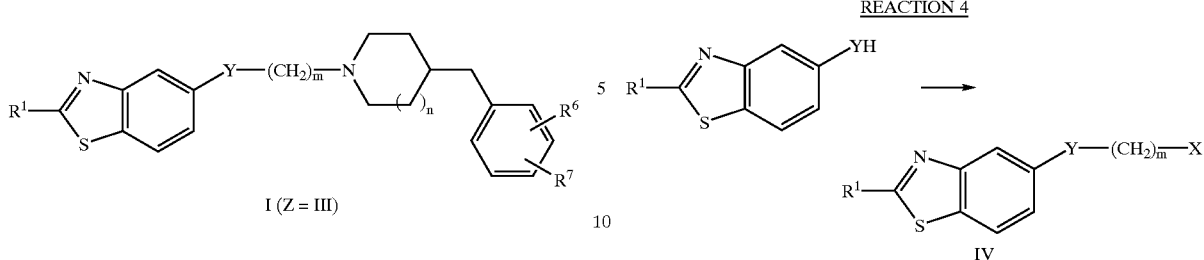

I (Z = III)

REACTION 4

REACTION 3

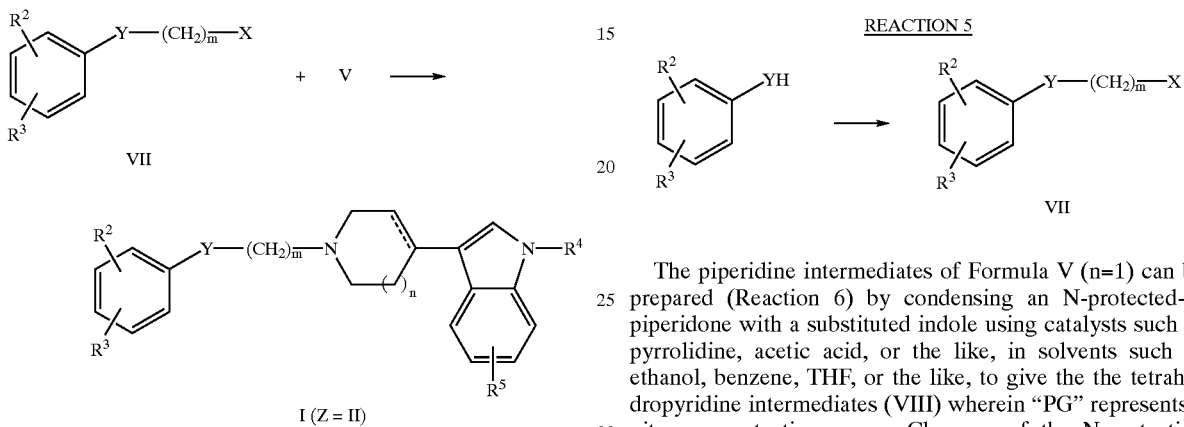

I (Z = II)

Intermediates of Formulas IV and VII are conveniently made by alkylating (Reactions 4, 5) appropriate benzothiazoles or benzenes with dihaloalkanes in solvents such as acetone, acetonitrile, DMSO, DMF, or the like, and in the presence of suitable bases, such as trialkyl amines or sodium, potassium, or cesium carbonate, or the like, under standard alkylation conditions.

REACTION 5

The piperidine intermediates of Formula V (n=1) can be prepared (Reaction 6) by condensing an N-protected-4-piperidone with a substituted indole using catalysts such as pyrrolidine, acetic acid, or the like, in solvents such as ethanol, benzene, THF, or the like, to give the the tetrahydropyridine intermediates (VIII) wherein "PG" represents a nitrogen protecting group. Cleavage of the N-protecting group provides the tetrahydropyridines of Formula Va. Alternatively, the tetrahydropyridine intermediates (VIII) can be reduced using using hydrogen and a suitable catalyst such as platinum, palladium, or ruthenium catalysts, in solvents such as ethanol, ethyl acetate, or the like, to give the piperidine intermediates (IX). The N-protecting group can then be cleaved using methods known to those skilled in the art to give the piperidine intermediates of Formula Vb.

REACTION 6

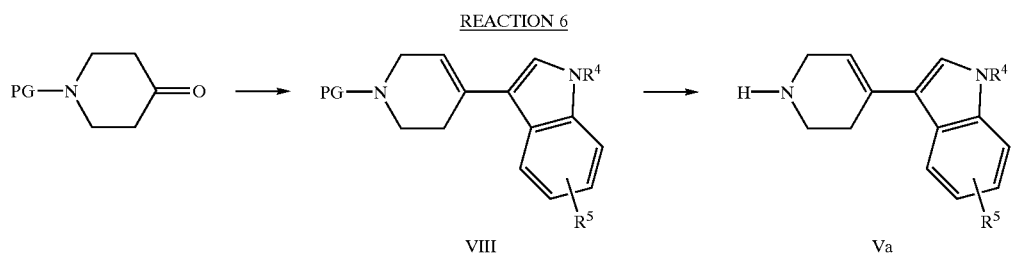

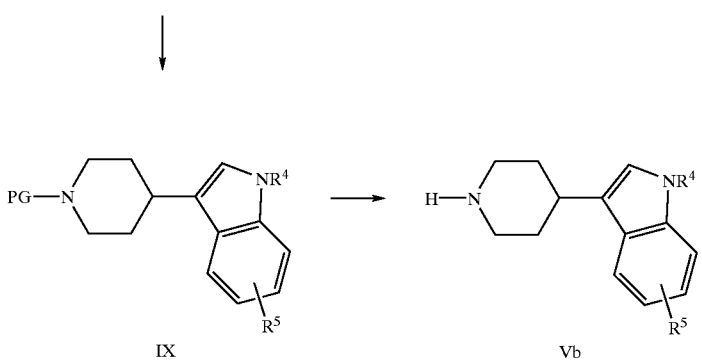

The piperidine intermediates of Formula VI are conveniently prepared by condensation of an N-protected-4-piperidone with reagents such as benzyl phosphonate esters using bases such as NaH, LDA, sodium or potassium alkoxides, or the like, in solvents such as THF, diethyl ether, or the like, to provide the benzylidene intermediate, XI. Subsequent reduction of the benzylidene group using hydrogen and platinum, palladium, or ruthenium catalysts, in solvents such as ethanol, ethyl acetate, or the like, provides the piperidine intermediate, X. The N-protecting group is then cleaved using methods known to those skilled in the art to give the piperidine intermediates of Formula II as depicted in Reaction 7.

REACTION 7

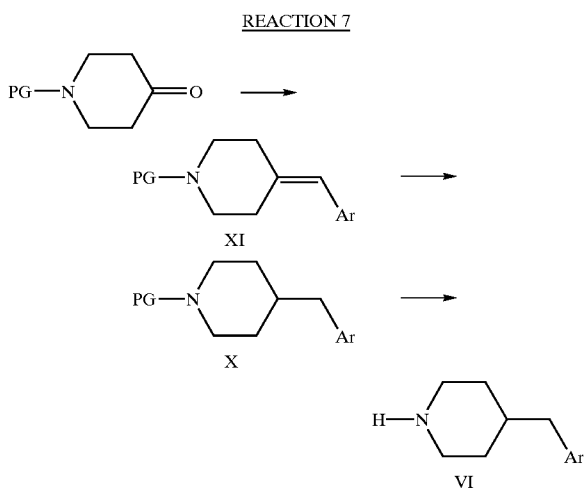

The reactions depicted above and their application are familiar to the practitioner skilled in organic synthesis and modifications of conditions and reagents would be readily understood. The skilled synthetic chemist would know how to adapt these processes for preparation of specific formula I compound including other compounds embraced by this invention but not specifically disclosed. Variations of the methods to produce the same compounds in somewhat different fashion will also be evident to one skilled in the art. To provide greater detail in description, representative synthetic examples are provided infra in the "Specific Embodiments" section.

The compounds of Formula I bind potently to the human 5-HT transporter and inhibit the re-uptake of endogenous serotonin. Selective serotonin reuptake inhibitors (SSRIs) are effective for the treatment of mental depression and have been reported to be useful for treating chronic pain (see: R. W. Fuller, Pharmacologic Modification of Serotonergic Function: Drugs for the Study and Treatment of Psychiatric and Other Disorders," *J. Clin. Psychiatry,* 47:4 (Suppl.) April 1986, pp. 4–8). Compounds of the present invention are also envisioned to be useful for treating psychosis, acute mania, mild anxiety states or depression with secondary psychotic episodes. The present compounds are also envisioned to be useful in treating obsessive-compulsive disorders, feeding disorders, anxiety disorders and panic disorders.

Like many clinically effective antipsychotic agents, the compounds of Formula I also are antagonists at the human $D_{2L}$ receptor as determined by [$^3$H]-spiperone binding studies using human $D_{2L}$ receptors stably expressed in HEK-293 cells. Clinical studies have demonstrated that selective serotonin reuptake inhibitors (SSRIs) augment the efficacy of traditional neuroleptic antipsychotic agents in improving negative symptoms in schizophrenic patients (Silver, et al., 1998, *J. Clin. Psychopharmacol.* 18:208; Goff, et al., 1994, *Psychopharmacology* 117:417). Therefore, the compounds of Formula I possess a unique serotonergic and dopaminergic profile, making the compounds of the present invention useful for treating psychosis, and in particular, the negative symptoms in schizophrenic patients.

Another aspect of the instant invention provides a method for treating a mammal afflicted with psychosis, depression, or chronic pain which comprises administering systemically to said mammal a therapeutically effective amount of a compound of formula I or a pharmaceutically acceptable acid addition salt thereof.

The administration and dosage regimen of compounds of Formula I are considered to be done in the same manner as for the reference compound fluoxetine, cf: Schatzberg, et al., *J. Clin. Psychopharmacology* 7/6 Suppl. (1987) pp. 4451–4495, and references therein. Although the dosage and dosage regimen must in each case be carefully adjusted, utilizing sound professional judgement and considering the age, weight and condition of the recipient, the route of administration and the nature and gravity of the illness, generally the daily dose will be from about 0.05 to about 10 mg/kg, preferably 0.1 to 2 mg/kg, when administered parenterally and from about 1 to about 50 mg/kg, preferably about 5 to 20 mg/kg, when administered orally. In some instances, a sufficient therapeutic effect can be obtained at lower doses while in others, larger doses will be required. Systemic administration refers to oral, rectal and parenteral (i.e. intramuscular, intravenous and subcutaneous). Generally, it will be found that when a compound of the present invention is administered orally, a larger quantity of the active agent is required to produce the same effect as a similar quantity given parenterally. In accordance with good clinical practice, it is preferred to administer the instant compounds at a concentration level that will produce effective antidepressant effects without causing any harmful or untoward side effects.

The compounds of the present invention may be administered for antipsychotic and antidepressant purposes either as individual therapeutic agents or as mixtures with other therapeutic agents. Therapeutically, they are generally given as pharmaceutical compositions comprised of an antidepressant amount of a compound of Formula I or a pharmaceutically acceptable salt thereof and a pharmaceutically acceptable carrier. Pharmaceutical compositions which provide from about 1 to 500 mg of the active ingredient per unit dose are preferred and are conventionally prepared as tablets, lozenges, capsules, powders, aqueous or oily suspensions, syrups, elixirs, and aqueous solutions.

The nature of the pharmaceutical composition employed will, of course, depend on the desired route of administration. For example, oral compositions may be in the form of tablets or capsules and may contain conventional excipients such as binding agents (e.g. starch) and wetting agents (e.g. sodium lauryl sulfate). Solutions or suspensions of a Formula I compound with conventional pharmaceutical vehicles are employed for parenteral compositions such as an aqueous solution for intravenous injection or an oily suspension for intramuscular injection.

Description of Specific Embodiments

The compounds which constitute this invention, their methods of preparation and their biologic actions will appear more fully from consideration of the following examples, which are given for the purpose of illustration only and are not to be construed as limiting the invention in sphere or scope. In the following examples, used to illustrate the foregoing synthetic processes, temperatures are expressed in degrees Celsius and melting points are uncorrected. The nuclear magnetic resonance (NMR) spectral characteristics refer to chemical shifts (δ) expressed as parts per million (ppm) versus tetramethylsilane (TMS) as reference standard. The relative area reported for the various shifts in the $^1$H NMR spectral data corresponds to the number of hydrogen atoms of a particular functional type in the molecule. The nature of the shifts as to multiplicity is reported as broad singlet (bs), singlet (s), multiplet (m), heptet (hept), quartet (q), triplet (t) or doublet (d). Abbreviations employed are DMSO-d$_6$ (deuterodimethylsulfoxide), CDCl$_3$ (deuterochloroform) and are otherwise conventional. The infrared (IR) spectral descriptions include only absorption wave numbers (cm$^{-1}$).

Analytical thin-layer chromatography (TLC) was performed on 0.25 mm EM silica gel 60 F-254 coated glass plates and preparative flash chromatography was performed on EM silica gel (36–62 μm). The solvent systems used are reported where appropriate. All reaction, extraction and chromatography solvents were reagent grade and used without further purification except tetrahydrofuran (THF) which was distilled from sodium/benzophenone ketyl. All non-aqueous reactions were carried out in flame-dried glassware under a nitrogen atmosphere.

Synthesis of Intermediates of Formula IV

EXAMPLE 1

2-methyl-5-(3-chloropropoxyl)-benzothiazole

A mixture of 2-methyl-5-benzothiazolol (8 g, 48.4 mmol), 1-bromo-3-chloropropane (23 g, 146 mmol), and potassium carbonate (33.6 g, 240 mmol) in 50 ml of acetonitrile was stirred at 60° C. for 18 hr. The mixture was cooled, evaporated under reduced pressure, diluted with water and ethyl acetate. The organic phase was separated, dried over sodium sulfate, and concentrated under vacuum to give 2-methyl-5-(3-chloropropoxyl)-benzothiazole (IV) as a tan crystalline solid (10 g, 85%, mp 63–65° C., MS (CI) m+1=242).

In a similar manner, phenols and thiophenols can be reacted with a dihaloalkane to produce the corresponding benzene intermediates of Formula VII.

Synthesis of Intermediates of Formula VI

EXAMPLE 2

4-(2-bromobenzyl)piperidine

A solution of dimethyl 2-bromobenzylphosphonate (45.66 g, 148.9 mmol) in THF was added slowly to a mixture of NaH (7.14 g of a 60% mineral oil dispersion, 178.5 mmol) in THF (200 ml) and the mixture was stirred for 1 hr. A solution of 1-(tert-butoxycarbonyl)-4-piperidinone (29.67 g, 148.9 mmol) in THF was added dropwise and the mixture was heated to reflux for 1.5 hr. The mixture was cooled and quenched with brine. The mixture was diluted with ethyl acetate, washed with water, and dried with brine. The organic layer was concentrated in vacuo to an oil. The oil was dissolved in acetonitrile and extracted with hexane. The acetonitrile layer was concentrated in vacuo to give 1-(tert-butoxycarbonyl)-4-[(2-bromophenyl)methylene]piperidine (XI) as an oil that solidified upon standing (48.3 g, 97%).

A solution of 1-(tert-butoxycarbonyl)-4-[(2-bromophenyl)methylene]-piperidine (XI, 8 g, 22.7 mmole) in ethyl acetate (75 ml) and ethanol (75 ml) was shaken with PtO$_2$ (0.75 g) and hydrogen (60 psi) for 15 min. Two further batches of 1-(tert-butoxycarbonyl)-4-[(2-bromophenyl)-methylene]-piperidine (8 g each, 24 g total) were similarly reduced and the mixtures were filtered. The filtrates were combined and concentrated in vacuo. The residue (X) was dissolved in dioxane (200 ml) and 3N HCl (100 ml) and stirred for 18 hr. The solution was concentrated in vacuo and the residue was made basic with 50% sodium hydroxide. The mixture was extracted with CH$_2$Cl$_2$. The extracts were dried over Na$_2$SO$_4$ and concentrated in vacuo to give a yellow oil that was purified by short path vacuum distillation to give 4-(2-bromobenzyl)piperidine (VI) as a oil (15 g, 86.6%). The oil converted to the fumarate salt using fumaric acid (6.85 g) in 2-propanol to give 4-(2-bromobenzyl) piperidine fumarate as a white solid (15.8 g, 62.6% overall, mp: 164–165° C.).

Also prepared by this general method were:

4-(2-bromo-5-fluorobenzyl)piperidine;
4-(2-bromo-5-methoxybenzyl)piperidine;
4-(2,5-dichlorobenzyl)piperidine; and
4-(2-chlorobenzyl)piperidine.

Synthesis of Intermediates of Formula V

EXAMPLE 3

3-(4-Piperidinyl)-5-cyanoindole (V)

A. 3-[1-(t-butoxycarbonyl)-1,2,3,6-tetrahydro-4-pyridinyl]-5-cyanoindole (VIII)

A stirred solution of 5-cyanoindole (10.0 g, 70.3 mmol), t-butyl-4-oxo-1-piperidinecarboxylate (15.4 g, 77.3 mmol), and pyrrolidine (14.7 mL, 175.7 mmol) in ethanol (200 mL) was heated at reflux for 20 hours then cooled to 0° C. The resulting precipitate was collected by vacuum filtration and rinsed with cold ethanol and hexanes to afford the product as a white solid (15.4 g, 68%).

B. 3-[1-(t-butoxycarbonyl)-4-piperidinyl]-5-cyanoindole (IX)

A solution of 3-[1-(t-butoxycarbonyl)-1,2,3,6-tetrahydro-pyridin-4-yl]-5-cyanoindole (15.3 g, 47.3 mmol) in ethanol was treated with 10% palladium on carbon (2.38 g). The mixture was hydrogenated on a Parr shaker at 50 psi for 18 hours and then filtered through celite to remove inorganics. Evaporation gave the desired product as an off white solid (15.2 g, 98%). $^1$H-NMR δ(CDCl$_3$) 8.33 (br s, 1 H), 7.99 (s, 1 H), 7.42 (s, 2 H), 7.07 (s, 1 H), 4.22 (m, 2 H), 2.82 (m, 3 H), 1.98 (br d, 2 H), 1.66 (m, 2 H), 1.48 (s, 9 H).

C. 3-(4-piperidinyl)-5-cyanoindole (Vb)

A stirred solution of 3-[1-(t-butoxycarbonyl)-4-piperidyl]-5-cyanoindole (8.4 g, 25.8 mmol) in methanol (260 mL) was treated with 4N hydrochloric acid in dioxane (64 mL, 256 mmol). After stirring at ambient temperature for 2 hours, the solution was concentrated. The residue was neutralized with 1N NaOH, extracted with ethyl acetate, dried, and concentrated to afford the product as a white solid (5.29 g, 91%). $^1$H-NMR δ(CDCl$_3$) 8.59 (br s, 1 H), 8.00 (s, 1 H), 7.40 (s, 2 H), 7.09 (s, 1 H), 3.23 (br d, 1 H), 2.93 (m, 1 H), 2.81 (br t, 2 H), 2.01 (m, 2 H), 1.66 (m, 4 H).

By using VIII instead of IX in the hydrolysis reaction (C), the corresponding tetrahydropyridine intermediate Va is produced.

By starting with an appropriate VIII intermediate and using the procedures of Example 3, selected Va and/or Vb intermediates are readily prepared. A number of descriptive preparations of assorted Formula VIII intermediates follow.

A. 3-[1-(t-butoxycarbonyl)-1,2,3,6-tetrahydro-4-pyridinyl]-4-fluoroindole

A stirred solution of 4-fluoroindole (400 mg, 3.0 mmol), t-butyl-4-oxo-1-piperidinecarboxylate (650 mg, 3.3 mmol), and pyrrolidine (0.62 mL, 7.4 mmol) in ethanol (10 mL) was heated at reflux for 16 hours. Solvent was evaporated and the residue subjected to chromatography on silica gel with 20% ethyl acetate/hexanes to afford a yellow solid (250 mg, 27%).

B. 3-[1-(t-butoxycarbonyl)-1,2,3,6-tetrahydro-4-pyridinyl]-7-fluoroindole

A stirred solution of 7-fluoroindole (400 mg, 3.0 mmol), t-butyl-4-oxo-1-piperidinecarboxylate (650 mg, 3.3 mmol), and pyrrolidine (0.62 mL, 7.4 mmol) in ethanol (10 mL) was heated at reflux for 16 hours. Solvent was evaporated and the residue subjected to chromatography on silica gel with 20% ethyl acetate/hexanes to afford a yellow solid (620 mg, 66%).

C. 3-[1-(t-butoxycarbonyl)-1,2,3,6-tetrahydro-4-pyridinyl]-5-chloroindole

A stirred solution of 5-chloroindole (455 mg, 3.0 mmol), t-butyl-4-oxo-1-piperidinecarboxylate (650 mg, 3.3 mmol), and pyrrolidine (0.62 mL, 7.4 mmol) in ethanol (10 mL) was heated at reflux for 16 hours. Solvent was evaporated and the residue subjected to chromatography on silica gel with 20% ethyl acetate/hexanes to afford a yellow solid (752 mg, 75%).

D. 3-[1-(t-butoxycarbonyl)-1,2,3,6-tetrahydro-4-pyridinyl]-6-chloroindole

A stirred solution of 6-chloroindole (455 mg, 3.0 mmol), t-butyl-4-oxo-1-piperidinecarboxylate (650 mg, 3.3 mmol), and pyrrolidine (0.62 mL, 7.4 mmol) in ethanol (10 mL) was heated at reflux for 16 hours. Solvent was evaporated and the residue was recrystallized from ethyl acetate and hexanes to afford a yellow solid (721 mg, 72%).

E. 3-[1-(t-butoxycarbonyl)-1,2,3,6-tetrahydro-4-pyridinyl]-6-bromoindole

A stirred solution of 6-bromoindole (390 mg, 2.0 mmol), t-butyl-4-oxo-1-piperidinecarboxylate (438 mg, 2.2 mmol), and pyrrolidine (0.42 mL, 5.0 mmol) in ethanol (10 mL) was heated at reflux for 16 hours. Solvent was evaporated and the residue subjected to chromatography on silica gel with 20% ethyl acetate/hexanes to afford a yellow solid (354 mg, 47%).

F. 3-[1-(t-butoxycarbonyl)-1,2,3,6-tetrahydro-4-pyridinyl]-7-bromoindole

A stirred solution of 7-bromoindole (390 mg, 2.0 mmol), t-butyl-4-oxo-1-piperidinecarboxylate (438 mg, 2.2 mmol), and pyrrolidine (0.42 mL, 5.0 mmol) in ethanol (10 mL) was heated at reflux for 16 hours. Solvent was evaporated and the residue subjected to chromatography on silica gel with 20% ethyl acetate/hexanes to afford a yellow solid (215 mg, 29%).

Synthesis of Compounds of Formula I
A. Benzene Derivatives

EXAMPLE 4

3-[1-(3-phenoxypropyl)-4-piperidinyl]-5-cyanoindole

A stirred solution of 3-(4-piperidinyl)-5-cyanoindole (0.71 g, 2.2 mmol), 3-phenoxypropyl bromide (0.52 g, 2.4 mmol), and triethylamine (0.6 ml, 4.4 mmol) in methanol (10 mL) was heated at reflux for 18 hours. The solution was concentrated in vacuo. Purification by flash chromatography yielded the product (0.35 g, 44%). $^1$H-NMR $\delta$(CD$_3$OD) 8.11 (s, 1 H), 7.49 (d, 1 H), 7.40 (d, 1 H), 7.28 (m, 3 H), 6.94 (m, 3 H), 4.12 (t, 2 H), 3.59 (br d, 2 H), 3.26–3.18 (m, 3 H), 3.04 (br t, 2 H), 2.25 (m, 4 H), 2.02 (br q, 2 H).

The following compounds were prepared essentially as described for the previous preparation:

EXAMPLE 5

3-{1-[3-(2-fluorophenoxy)propyl]-4-piperidinyl}-5-cyanoindole $^1$H-NMR $\delta$(CD$_3$OD) 8.10 (s, 1 H), 7.49 (d, 1 H), 7.37 (s, 1 H), 7.26 (s, 1 H), 7.12 (m, 3 H), 6.93 (m, 1 H), 4.19 (t, 2 H), 3.46 (br d, 2 H), 3.18 (m, 3 H), 2.80 (br t, 2 H), 2.20 (m, 4 H), 2.00 (br q, 2 H).

EXAMPLE 6

3-{1-[3-(4-fluorophenoxy)propyl]-4-piperidinyl}-5-cyanoindole $^1$H-NMR $\delta$(CD$_3$OD) 8.10 (s, 1 H), 7.48 (d, 1 H), 7.39 (d, 1 H), 7.27 (s, 1 H), 7.01 (m, 2 H), 6.92 (m, 2 H), 4.06 (t, 2 H), 3.46 (br d, 2 H), 3.07 (m, 3 H), 2.81 (br t, 2 H), 2.19 (m, 4 H), 1.98 (br q, 2 H).

EXAMPLE 7

3-{1-[3-(2-methoxyphenoxy)propyl]-4-piperidinyl}-5-cyanoindole $^1$H-NMR $\delta$(CD$_3$OD) 8.10 (s, 1 H), 7.49 (d, 1 H), 7.38 (d, 1 H), 7.28 (s, 1 H), 6.95 (m, 4 H), 4.13 (t, 2 H), 3.83 (s, 3 H), 3.52 (br d, 2 H), 3.13 (m, 3 H), 2.85 (br t, 2 H), 2.22 (m, 4 H), 1.99 (br q, 2 H).

EXAMPLE 8

3-{1-[3-(3-methoxyphenoxy)propyl]-4-piperidinyl}-5-cyanoindole $^1$H-NMR $\delta$(CD$_3$OD) 8.08 (s, 1 H), 7.47 (d, 1 H), 7.36 (d, 1 H), 7.22 (s, 1 H), 7.15 (t, 1 H), 6.50 (m, 3 H), 4.03 (t, 2 H), 3.76 (s, 3 H), 3.18 (br d, 2 H), 2.89 (m, 1 H), 2.69 (m, 2 H), 2.33 (br t, 2 H), 2.05 (m, 4 H), 1.88 (br q, 2 H).

EXAMPLE 9

3-{1-[3-(4-methoxyphenoxy)propyl]-4-piperidinyl}-5-cyanoindole $^1$H-NMR $\delta$(CD$_3$OD) 8.10 (s, 1 H), 7.49 (d, 1 H), 7.38 (d, 1 H), 7.28 (s, 1 H), 6.86 (m, 4 H), 4.05 (t, 2 H), 3.74 (s, 3 H), 3.52 (br d, 2 H), 3.13 (m, 3 H), 2.90 (br t, 2 H), 2.18 (m, 4 H), 1.98 (br q, 2 H).

EXAMPLE 10

3-{1-[3-(3,4-dimethoxyphenoxy)propyl]-4-piperidinyl}-5-cyanoindole $^1$H-NMR $\delta$(CD$_3$OD) 8.09 (s, 1 H), 7.48 (d, 1 H), 7.38 (d, 1 H), 7.25 (s, 1 H), 6.85 (d, 1 H), 6.59 (s, 1 H), 6.46 (dd, 1

H), 4.02 (t, 2 H), 3.81 (s, 3 H), 3.78 (s, 3 H), 3.34 (br d, 2H), 3.00 (m, 1 H), 2.89 (t, 2 H), 2.59 (br t, 2 H), 2.10 (m, 4 H), 1.92 (br q, 2 H).

B. Benzothiazole Derivatives

EXAMPLE 11

5-{3-[4-(4-fluoroindol-3-yl)-1,2,5,6-tetrahydropyrid-1-yl]propoxy}-2-methylbenzothiazole To a solution of 3-[1-(t-butoxycarbonyl)-1,2,3,6-tetrahydro-4-pyridinyl]-4-fluoroindole (47 mg, 0.15 mmol) in dichloromethane (2 mL) was added hydrochloric acid (1 mL, 4N in dioxane, 4 mmol). This mixture was stirred for 2 hours and was then evaporated to dryness. To this was added methanol (2 mL) and triethylamine (0.1 mL, 0.73 mmol) and this solution was transferred to a glass vial containing 1-(3-(2-methyl-5-benzothiazoxy)-bromopropane (43 mg, 0.15 mmol). The reaction was sealed and heated at 65° C. for 2 days. The reaction was filtered and purified on a Shimadzu preparative HPLC system with the following conditions:

Reverse Phase Column 30×75 mm; start % B=20; final % B=100; gradient time=12 min; flow rate=40 mL/min; wavelength=220 nm.

The product was evaporated to dryness and the TFA salt was obtained as an orange oil (30 mg, 38%).

$^1$H-NMR δ (CDCl$_3$) 2.37 (m, 2H), 2.79 (bd, J=16 Hz, 1H), 2.92 (s, 3H), 3.01 (m, 1H), 3.28 (m, 1H), 3.44 (m, 2H), 3.64 (bd, J=16.2 Hz, 1H), 3.76 (m, 1H), 4.15(t, J=5.5 Hz, 2H), 4.23 (bd, J=16.1 Hz, 1H), 5.83 (bs, 1H), 5.98 (s, 1H), 6.78 (dd, J=11.5, 7.7 Hz, 1H), 7.03–7.18 (m, 3H), 7.57 (s, 1H), 7.69 (d, J=8.8 Hz, 1H), 8.95 (s, 1H).

EXAMPLE 12

5-{3-[4-(5-cyanoindol-3-yl)-1,2,5,6-tetrahydropyrid-1-yl]propoxy}-2-methylbenzothiazole A mixture of 2-methyl-5-(3-chloropropoxyl)-benzothiazole (3 g, 12.4 mmol), 5-cyano-3-(1,2,3,6-tetrahydropyridin-4-yl)-1H-indole (3 g, 13.4 mmol) and a catalytic amount of potassium iodide in 50 ml of acetonitrile was stirred at 80° C. overnight. The reaction mixture was cooled, diluted with water, ammonium hydroxide and ethyl acetate. The two phases were separated and the aqueous phase was extracted with ethyl acetate twice. The organic phases were combined, washed with brined, dried over sodium sulfate and then concentrated under reduced pressure to a solid. This residual solid was subjected to a silica gel chromatography, eluting with 7% methanol in dichloromethane. Fractions shown to contain product were combined and concentrated to provide 2 g of the title compound in 35% yield as free base. The resulting free base was dissolved in methanol/dichloromethane and precipitated with excess HCl in ether. Recrystalization from ethanol give 1.8 g of the title compound as a light yellow solid. mp. 263–65° C. MS(CI) m+1=429. EA (C$_{25}$H$_{24}$N$_4$OS.1.7HCl): Theory: C, 61.21%; H, 5.28%; N, 11.42%. Found: C, 61.10%; H, 5.43%; N, 11.39%.

Also prepared by this general method from the appropriate starting materials were:

EXAMPLE 13

5-{4-[4-(4-fluoroindol-3-yl)1,2,5,6-tetrahydropyrid-1-yl]butoxy}-2-methylbenzothiazole

EXAMPLE 14

5-{5-[4-(4-fluoroindol-3-yl)-1,2,5,6-tetrahydropyrid-1-yl]pentoxy}-2-methylbenzothiazole

EXAMPLE 15

5-{4-[4-(5-fluoroindol-3-yl)1,2,5,6-tetrahydropyrid-1-yl]butoxy}-2-methylbenzothiazole

EXAMPLE 16

5-{5-[4-(5-fluoroindol-3-yl)-1,2,5,6-tetrahydropyrid-1-yl]pentoxy}-2-methylbenzothiazole

EXAMPLE 17

5-{3-[4-(7-fluoroindol-3-yl)-1,2,5,6-tetrahydropyrid-1-yl]propoxy}-2-methylbenzothiazole

EXAMPLE 18

5-{4-[4-(7-fluoroindol-3-yl)1,2,5,6-tetrahydropyrid-1-yl]butoxy}-2-methylbenzothiazole

EXAMPLE 19

5-{5-[4-(7-fluoroindol-3-yl)-1,2,5,6-tetrahydropyrid-1-yl]pentoxy}-2-methylbenzothiazole

EXAMPLE 20

5-{4-[4-(5-chloroindol-3-yl)1,2,5,6-tetrahydropyrid-1-yl]butoxy}-2-methylbenzothiazole

EXAMPLE 21

5-{5-[4-(5-chloroindol-3-yl)-1,2,5,6-tetrahydropyrid-1-yl]pentoxy}-2-methylbenzothiazole

EXAMPLE 22

5-{3-[4-(6-chloroindol-3-yl)-1,2,5,6-tetrahydropyrid-1-yl]propoxy}-2-methylbenzothiazole

EXAMPLE 23

5-{4-[4-(6-chloroindol-3-yl)1,2,5,6-tetrahydropyrid-1-yl]butoxy}-2-methylbenzothiazole

EXAMPLE 24

5-{5-[4-(6-chloroindol-3-yl)-1,2,5,6-tetrahydropyrid-1-yl]pentoxy}-2-methylbenzothiazole

EXAMPLE 25

5-{3-[4-(6-bromoindol-3-yl)-1,2,5,6-tetrahydropyrid-1-yl]propoxy}-2-methylbenzothiazole

EXAMPLE 26

5-{4-[4-(6-bromoindol-3-yl)1,2,5,6-tetrahydropyrid-1-yl]butoxy}-2-methylbenzothiazole

EXAMPLE 27

5-{5-[4-(6-bromoindol-3-yl)-1,2,5,6-tetrahydropyrid-1-yl]pentoxy}-2-methylbenzothiazole

EXAMPLE 28

5-{3-[4-(7-bromoindol-3-yl)-1,2,5,6-tetrahydropyrid-1-yl]propoxy}-2-methylbenzothiazole

EXAMPLE 29

5-{4-[4-(7-bromoindol-3-yl)1,2,5,6-tetrahydropyrid-1-yl]butoxy}-2-methylbenzothiazole

EXAMPLE 30

5-{5-[4-(7-bromoindol-3-yl)-1,2,5,6-tetrahydropyrid-1-yl]pentoxy}-2-methylbenzothiazole

EXAMPLE 31

5-{3-[4-(5-methoxyindol-3-yl)-1,2,5,6-tetrahydropyrid-1-yl]propoxy}-2-methylbenzothiazole

EXAMPLE 32

5-{4-[4-(5-methoxyindol-3-yl)1,2,5,6-tetrahydropyrid-1-yl]butoxy}-2-methylbenzothiazole

EXAMPLE 33

5-{5-[4-(5-methoxyindol-3-yl)-1,2,5,6-tetrahydropyrid-1-yl]pentoxy}-2-methylbenzothiazole

EXAMPLE 34

5-{3-[4-(5-fluoroindol-3-yl)-1,2,5,6-tetrahydropyrid-1-yl]propoxy}-2-methylbenzothiazole

EXAMPLE 35

5-{3-[4-(5-fluoroindol-3-yl)piperidinyl]propoxy}-2-methylbenzothiazole

EXAMPLE 36

5-{3-[4-(5-bromoindol-3-yl)-1,2,5,6-tetrahydropyrid-1-yl]propoxy}-2-methylbenzothiazole

EXAMPLE 37

5-{3-[4-(5-cyanoindol-3-yl)piperidinyl]propoxy}-2-methylbenzothiazole

EXAMPLE 38

5-{4-[4-(5-cyanoindol-3-yl)-1,2,5,6-tetrahydropyrid-1-yl]butoxy}-2-methylbenzothiazole

EXAMPLE 39

5-{4-[4-(5-cyanoindol-3-yl)piperidinyl]butoxy}-2-methylbenzothiazole; and

EXAMPLE 40

2-methyl-5-[3-[4-(2-bromo-5-fluorobenzyl)-piperidinyl]-propoxyl]-benzothiazole

The title compound was prepared in similar fashion from 2-methyl-5-(3-chloropropoxyl)-benzothiazole and 2-bromo-5-fluorobenzyl)-piperidine. The resulting free base (40% yield) was dissolved in ethyl acetate and precipitated with one equivalent of HCl in ether. mp. 217–20° C. MS(CI) m+1=477. EA ($C_{23}H_{26}BrFN_2OS \cdot HCl \cdot H_2O$): Theory: C, 51.94%; H, 5.50%; N, 5.27%. Found: C, 52.05%; H, 5.34%; N, 5.23%.

Also prepared by this general method from the appropriate starting materials were:

EXAMPLE 41

5-{3-[4-(2H-benzo[d]1,3-dioxolan-4-ylmethyl)piperidinyl]propoxy}-2-methylbenzothiazole

EXAMPLE 42

5-(3-{4-[(2-bromo-5-methoxyphenyl)methyl]piperidinyl}propoxy)-2-methylbenzothiazole

EXAMPLE 43

5-(3-{4-[(2-bromophenyl)methyl]piperidinyl}propoxy)-2-methylbenzothiazole

EXAMPLE 44

5-(3-{4-[(2-bromo-5-fluorophenyl)methyl]piperidinyl}propoxy)-2-methylbenzothiazole

EXAMPLE 45

5-(3-{4-[(2,-5-difluorophenyl)methyl]piperidinyl}propoxy)-2-methylbenzothiazole

EXAMPLE 46

5-(3-{4-[(3-methoxyphenyl)methyl]piperidinyl}propoxy)-2-methylbenzothiazole

EXAMPLE 47

5-(3-{4-[(2-chlorophenyl)methyl]piperidinyl}propoxy)-2-methylbenzothiazole; and

EXAMPLE 48

5-(3-{4-[(2,5-dichlorophenyl)methyl]piperidinyl}propoxy)-2-methylbenzothiazole

Dopamine Binding Protocol

HEK-293 cells that stably express recombinant human dopamine $D_{2L}$ receptors (HEK-$D_{2L}$ cells) were grown at 37° C. in 5% $CO_2$ as a monolayer in medium consisting of EMEM supplemented with 10% fetal bovine serum and G418 sulfate (500 μg/ml). To prepare membranes for radioligand binding experiments, cells were rinsed twice with phosphate-buffered saline (138 mM NaCl, 4.1 mM KCl, 5.1 mM $Na_2PO_4$, 1.5 mM $KH_2PO_2$ 11.1 mM glucose, pH 7.4), and incubated for 5–10 min. at 4° C. in hypotonic lysis buffer consisting of 10 mM Tris (pH 7.4) and 5 mM EDTA. Cells were transferred from plates to polypropylene tubes (16×100 mm), homogenized and centrifuged at 32,000×g for 20 min. Following centrifugation, pellets were resuspended by homogenization in buffer consisting of 50 mM Tris (pH 7.7 at 25° C.) and 1 mM EDTA. Homogenates were stored at −80° C. until needed. On the day of an experiment, homogenates were thawed then centrifuged at 32,000×g for 20 min. Following centrifugation, supernatants were discarded and pellets were resuspended in assay buffer consisting of 50 mM Tris (pH 7.4 at 25° C.), 1 mM EDTA and 6 mM $MgCl_2$. Membrane homogenates (~5 μg) were incubated with 150 pM [$^3$H]-spiperone (Amersham Life Science) and increasing concentrations of test compounds for 1.5 hours at 22° C. in a total volume of 400 μl. Reactions were stopped by addition of ice-cold assay buffer and filtration over glass fiber filters (Whatman GFB, pre-soaked in 0.05% polyethylenimine) using a microtitre format Brandel cell harvester. Filters were washed with 3 ml of ice-cold assay buffer. Non-specific binding was defined with 2 μM (+)butaclamol. Ki values were calculated using the method of Cheng and Prusoff (1973). Protein concentrations were determined by the method of Bradford (1976) with BSA as a standard.

Test data $IC_{50}$ values lower than 250 nM are considered to reflect affinity for dopamine $D_{2L}$ receptors. Compounds with $IC_{50}$ values lower than 100 nM comprise preferred compounds.

Serotonin Transporter Binding Assay

HEK-293 cells that stably express human serotonin transporters (HEK-hSERT cells) were grown at 37° C. in 5% $CO_2$ as a monolayer in medium consisting of EMEM supplemented with 10% fetal bovine serum and G418 sulfate (500 μg/ml). To prepare membranes for radioligand binding experiments, cells were rinsed twice with phosphate-buffered saline (138 mM NaCl, 4.1 mM KCl, 5.1 mM $Na_2PO_4$, 1.5 mM $KH_2O_4$, 11.1 mM glucose, pH 7.4). Cells were transferred from plates to polypropylene tubes (16×100 mm), centrifuged at 1,200×g for 5 min and were frozen at −80° C. until assay. Following centrifugation, pellets were resuspended by homogenization in buffer consisting of 50 mM Tris (pH 7.7 at 25° C.), 120 mM NaCl and 5 mM KCl and then centrifuged at 32,000×g for 10 min. Following centrifugation, supernatants were discarded and pellets were resuspended in buffer consisting of 50 mM Tris (pH 7.4 at 25° C.), 150 mM NaCl and 5 mM KCl. Membrane homogenates (200 μl/plate) were incubated with 1 nM [$^3$H]-citalopram (specific activity=85 Ci/mmol) and increasing concentrations of test compounds for 1 hour at 25° C. in a total volume of 250 μl. The assay buffer consisted of 50 mM Tris (pH 7.4 at 25° C.), 120 mM NaCl and 5 mM KCl (pH 7.4 with conc. HCl). Plates were incubated for 1 hour at 25° C., then filtered through 0.5% PEI treated Whatman GF/B filters using a Brandel cell harvester. Filters were washed three times with 3 ml of ice-cold tris wash buffer. Non-specific binding was defined with 10 μM fluoxetine. Amount of radioligand bound in the presence and absence of competitor was analyzed by plotting (−)log drug concentration versus the amount of radioligand specifically bound. The midpoint of the displacement curve ($IC_{50}$, nM), signifies the potency. $K_i$ values were calculated using the method of Cheng and Prusoff (1973).

Substances which inhibit the re-uptake of serotonin are recognized to be effective antidepressants (*Selective Serotonin Reuptake Inhibitors*. Edited by J P Feighner and W F Boyer, Chichester, England. John Wiley & Sons, 1991, pp 89–108). Test data $IC_{50}$ values lower than 250 nM are considered to reflect activity as an inhibitor of serotonin re-uptake. Compounds with $IC_{50}$ values lower than 100 nM comprise preferred compounds.

The following compounds of Formula I inhibit the re-uptake of serotonin with Ki lower than 100 nM, and are dopamine $D_{2L}$ ligands with Ki lower than 100 nM:

5-{3-[4-(5-fluoroindol-3-yl)-1,2,5,6-tetrahydropyrid-1-yl]propoxy}-2-methylbenzothiazole;

5-{3-[4-(5-cyanoindol-3-yl)-1,2,5,6-tetrahydropyrid-1-yl]propoxy}-2-methylbenzothiazole;

5-{3-[4-(5-fluoroindol-3-yl)piperidinyl]propoxy}-2-methylbenzothiazole;

5-{3-[4-(5-cyanoindol-3-yl)piperidinyl]propoxy}-2-methylbenzothiazole;

5-{4-[4-(5-cyanoindol-3-yl)-1,2,5,6-tetrahydropyrid-1-yl]butoxy}-2-methylbenzothiazole;

5-{4-[4-(5-cyanoindol-3-yl)piperidinyl]butoxy}2-methylbenzothiazole;

5-{3-[4-(5-bromoindol-3-yl)-1,2,5,6-tetrahydropyrid-1-yl]propoxy}-2-methylbenzothiazole;

5-{3-[4-(2H-benzo[d]1,3-dioxolan-4-ylmethyl)piperidinyl]propoxy}-2-methylbenzothiazole;

5-(3-{4-[(2-bromo-5-methoxyphenyl)methyl]piperidinyl}propoxy)-2-methylbenzothiazole;

5-(3-{4-[(2-bromophenyl)methyl]piperidinyl}propoxy)-2-methylbenzothiazole;

5-(3-{4-[(2-bromo-5-fluorophenyl)methyl]piperidinyl}propoxy)-2-methylbenzothiazole;

5-(3-{4-[(2,-5-difluorophenyl)methyl]piperidinyl}propoxy)-2-methylbenzothiazole;

5-(3-{4-[(3-methoxyphenyl)methyl]piperidinyl}propoxy)-2-methylbenzothiazole;

5-(3-{4-[(2-chlorophenyl)methyl]piperidinyl}propoxy)-2-methylbenzothiazole;

5-(3-{4-[(2,5-dichlorophenyl)methyl]piperidinyl}propoxy)-2-methylbenzothiazole;

3-[1-(3-phenoxypropyl)-4-piperidinyl]-5-cyanoindole;

3-{1-[3-(4-fluorophenoxy)propyl]-4-piperidinyl}-5-cyanoindole;

3-{1-[3-(2-fluorophenoxy)propyl]-4-piperidinyl}-5-cyanoindole;

3-{1-[3-(2-methoxyphenoxy)propyl]-4-piperidinyl}-5-cyanoindole;

3-{1-[3-(3-methoxyphenoxy)propyl]-4-piperidinyl}-5-cyanoindole;

3-{1-[3-(4-methoxyphenoxy)propyl]-4-piperidinyl}-5-cyanoindole;
3-{1-[3-(3,4-dimethoxyphenoxy)propyl]-4-piperidinyl}-5-cyanoindole;
5-{3-[4-(4-fluoroindol-3-yl)-1,2,5,6-tetrahydropyrid-1-yl]propoxy}-2-methylbenzothiazole;
5-{3-[4-(7-fluoroindol-3-yl)-1,2,5,6-tetrahydropyrid-1-yl]propoxy}-2-methylbenzothiazole;
5-{3-[4-(6-chloroindol-3-yl)-1,2,5,6-tetrahydropyrid-1-yl]propoxy}-2-methylbenzothiazole;
5-{3-[4-(6-bromoindol-3-yl)-1,2,5,6-tetrahydropyrid-1-yl]propoxy}-2-methylbenzothiazole;
5-{3-[4-(7-bromoindol-3-yl)-1,2,5,6-tetrahydropyrid-1-yl]propoxy}-2-methylbenzothiazole;
5-{3-[4-(5-methoxyindol-3-yl)-1,2,5,6-tetrahydropyrid-1-yl]propoxy}-2-methylbenzothiazole;
5-{4-[4-(4-fluoroindol-3-yl)1,2,5,6-tetrahydropyrid-1-yl]butoxy}-2-methylbenzothiazole;
5-{4-[4-(5-fluoroindol-3-yl)1,2,5,6-tetrahydropyrid-1-yl]butoxy}-2-methylbenzothiazole;
5-{4-[4-(7-fluoroindol-3-yl)1,2,5,6-tetrahydropyrid-1-yl]butoxy}-2-methylbenzothiazole;
5-{4-[4-(5-chloroindol-3-yl)1,2,5,6-tetrahydropyrid-1-yl]butoxy}-2-methylbenzothiazole;
5-{4-[4-(6-chloroindol-3-yl)1,2,5,6-tetrahydropyrid-1-yl]butoxy}-2-methylbenzothiazole;
5-{4-[4-(6-bromoindol-3-yl)1,2,5,6-tetrahydropyrid-1-yl]butoxy}-2-methylbenzothiazole;
5-{4-[4-(7-bromoindol-3-yl) 1,2,5,6-tetrahydropyrid-1-yl]butoxy}-2-methylbenzothiazole;
5-{5-[4-(4-fluoroindol-3-yl)-1,2,5,6-tetrahydropyrid-1-yl]pentoxy}-2-methylbenzothiazole;
5-{5-[4-(5-fluoroindol-3-yl)-1,2,5,6-tetrahydropyrid-1-yl]pentoxy}-2-methylbenzothiazole;
5-{5-[4-(7-fluoroindol-3-yl)-1,2,5,6-tetrahydropyrid-1-yl]pentoxy}-2-methylbenzothiazole;
5-{5-[4-(5-chloroindol-3-yl)-1,2,5,6-tetrahydropyrid-1-yl]pentoxy}-2-methylbenzothiazole;
5-{5-[4-(6-chloroindol-3-yl)-1,2,5,6-tetrahydropyrid-1-yl]pentoxy}-2-methylbenzothiazole;
5-{5-[4-(6-bromoindol-3-yl)-1,2,5,6-tetrahydropyrid-1-yl]pentoxy}-2-methylbenzothiazole;
5-{5-[4-(7-bromoindol-3-yl)-1,2,5,6-tetrahydropyrid-1-yl]pentoxy}-2-methylbenzothiazole;
5-{5-[4-(5-methoxyindol-3-yl)-1,2,5,6-tetrahydropyrid-1-yl]pentoxy}-2-methylbenzothiazole.

What is claimed is:

1. A compound of Formula I and its pharmaceutically acceptable salts

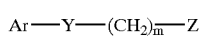

wherein:

Ar is 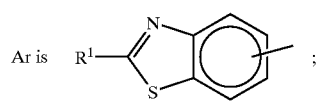 ;

Y is selected from oxygen and sulfur;

Z is selected from II and III;

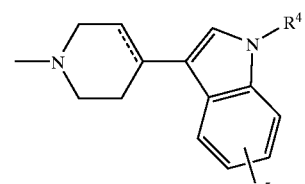

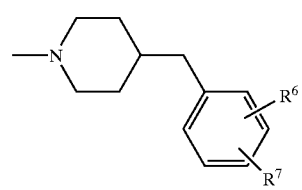

$R^1$ and $R^4$ are independently selected from hydrogen and lower alkyl;
$R^5$ is selected from hydrogen, halogen, lower alkoxy and cyano;
$R^8$ and $R^7$ are independently selected from hydrogen, halogen, and lower alkoxy;
m is an integer from 2 to 6;
and a dotted line represents an optional double bond.

2. A compound of claim 2 wherein Z is II.
3. A compound of claim 2 wherein Z is III.
4. A compound of claim 2 selected from:
5-{3-[4-(5-fluoroindol-3-yl)-1,2,5,6-tetrahydropyrid-1-yl]propoxy}-2-methylbenzothiazole;
5-{3-[4-(5-cyanoindol-3-yl)-1,2,5,6-tetrahydropyrid-1-yl]propoxy}-2-methylbenzothiazole;
5-{3-[4-(5-fluoroindol-3-yl)piperidinyl]propoxy}-2-methylbenzothiazole;
5-{3-[4-(5-cyanoindol-3-yl)piperidinyl]propoxy}-2-methylbenzothiazole;
5-{4-[4-(5-cyanoindol-3-yl)-1,2,5,6-tetrahydropyrid-1-yl]butoxy}-2-methylbenzothiazole;
5-{4-[4-(5-cyanoindol-3-yl)piperidinyl]butoxy}-2-methylbenzothiazole;
5-{3-[4-(5-bromoindol-3-yl)-1,2,5,6-tetrahydropyrid-1-yl]propoxy}-2-methylbenzothiazole;
5-{3-[4-(4-fluoroindol-3-yl)-1,2,5,6-tetrahydropyrid-1-yl]propoxy}-2-methylbenzothiazole;
5-{4-[4-(4-fluoroindol-3-yl)1,2,5,6-tetrahydropyrid-1-yl]butoxy}-2-methylbenzothiazole;
5-{5-[4-(4-fluoroindol-3-yl)-1,2,5,6-tetrahydropyrid-1-yl]pentoxy}-2-methylbenzothiazole;
5-{4-[4-(5-fluoroindol-3-yl)1,2,5,6-tetrahydropyrid-1-yl]butoxy}-2-methylbenzothiazole;
5-{5-[4-(5-fluoroindol-3-yl)-1,2,5,6-tetrahydropyrid-1-yl]pentoxy}-2-methylbenzothiazole;
5-{3-[4-(7-fluoroindol-3-yl)-1,2,5,6-tetrahydropyrid-1-yl]propoxy}-2-methylbenzothiazole;
5-{4-[4-(7-fluoroindol-3-yl)1,2,5,6-tetrahydropyrid-1-yl]butoxy}-2-methylbenzothiazole;
5-{5-[4-(7-fluoroindol-3-yl)-1,2,5,6-tetrahydropyrid-1-yl]pentoxy}-2-methylbenzothiazole;
5-{4-[4-(5-chloroindol-3-yl)1,2,5,6-tetrahydropyrid-1-yl]butoxy}-2-methylbenzothiazole;
5-{5-[4-(5-chloroindol-3-yl)-1,2,5,6-tetrahydropyrid-1-yl]pentoxy}-2-methylbenzothiazole;
5-{3-[4-(6-chloroindol-3-yl)-1,2,5,6-tetrahydropyrid-1-yl]propoxy}-2-methylbenzothiazole;
5-{4-[4-(6-chloroindol-3-yl)1,2,5,6-tetrahydropyrid-1-yl]butoxy}-2-methylbenzothiazole;

5-{5-[4-(6-chloroindol-3-yl)-1,2,5,6-tetrahydropyrid-1-yl]pentoxy}-2-methylbenzothiazole;
5-{3-[4-(6-bromoindol-3-yl)-1,2,5,6-tetrahydropyrid-1-yl]propoxy}-2-methylbenzothiazole;
5-{4-[4-(6-bromoindol-3-yl)1,2,5,6-tetrahydropyrid-1-yl]butoxy}-2-methylbenzothiazole;
5-{5-[4-(6-bromoindol-3-yl)-1,2,5,6-tetrahydropyrid-1-yl]pentoxy}-2-methylbenzothiazole;
5-{3-[4-(7-bromoindol-3-yl)-1,2,5,6-tetrahydropyrid-1-yl]propoxy}-2-methylbenzothiazole;
5-{4-[4-(7-bromoindol-3-yl)1,2,5,6-tetrahydropyrid-1-yl]butoxy}-2-methylbenzothiazole;
5-{5-[4-(7-bromoindol-3-yl)-1,2,5,6-tetrahydropyrid-1-yl]pentoxy}-2-methylbenzothiazole;
5-{3-[4-(5-methoxyindol-3-yl)-1,2,5,6-tetrahydropyrid-1-yl]propoxy}-2-methylbenzothiazole;
5-{4-[4-(5-methoxyindol-3-yl)1,2,5,6-tetrahydropyrid-1-yl]butoxy}-2-methylbenzothiazole; and
5-{5-[4-(5-methoxyindol-3-yl)-1,2,5,6-tetrahydropyrid-1-yl]pentoxy}-2-methylbenzothiazole.

5. A compound of claim 3 selected from:
5-(3-{4-[(2-bromo-5-methoxyphenyl)methyl]piperidinyl}propoxy)-2-methylbenzothiazole;
5-(3-{4-[(2-bromophenyl)methyl]piperidinyl}propoxy)-2-methylbenzothiazole;
5-(3-{4-[(2-bromo-5-fluorophenyl)methyl]piperidinyl}propoxy)-2-methylbenzothiazole;
5-(3-{4-[(2,-5-difluorophenyl)methyl]piperidinyl}propoxy)-2-methylbenzothiazole;
5-(3-{4-[(3-methoxyphenyl)methyl]piperidinyl}propoxy)-2-methylbenzothiazole;
5-(3-{4-[(2-chlorophenyl)methyl]piperidinyl}propoxy)-2-methylbenzothiazole; and
5-(3-{4-[(2,5-dichlorophenyl)methyl]piperidinyl}propoxy)-2-methylbenzothiazole.

6. A method for treating a patient suffering from psychosis, acute mania, or depression in combination with psychotic episodes, comprising administration to the patient of a therapeutically effective amount of a compound of Formula IA and its pharmaceutically acceptable salts.

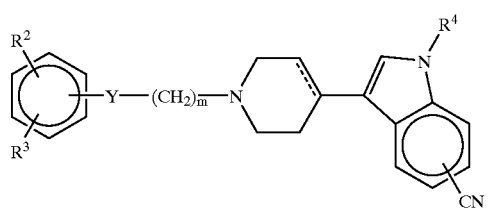

IA wherein:
Y is sulfur or oxygen;
$R^4$ is selected from H and lower alkyl;
$R^2$ and $R^3$ are independently selected from H, halogen, and lower alkoxy;
m is an integer from 2–6;
and a dotted line represents an optional double bond.

7. The method of claim 6 wherein the Formula IA compound is selected from:

3-[1-(3-phenoxypropyl)-4-piperidinyl]-5-cyanoindole;
3-{1-[3-(2-fluorophenoxy)propyl]-4-piperidinyl}-5-cyanoindole;
3-{1-[3-(4-fluorophenoxy)propyl]-4-piperidinyl}-5-cyanoindole;
3-{1-[3-(2-methoxyphenoxy)propyl]-4-piperidinyl}-5-cyanoindole;
3-{1-[3-(3-methoxyphenoxy)propyl]-4-piperidinyl}-5-cyanoindole;
3-{1-[3-(4-methoxyphenoxy)propyl]-4-piperidinyl}-5-cyanoindole; and
3-{1-[3-(3,4-dimethoxyphenoxy)propyl]-4-piperidinyl}-5-cyanoindole.

8. A method for treating a patient suffering from psychosis, acute mania, or depression in combination with psychotic episodes, comprising administration to the patient of a therapeutically effective amount of a compound of claim 1.

9. A pharmaceutical composition comprising an antipsychotic amount of a compound of claim 1 and a pharmaceutically acceptable carrier.

* * * * *